(12) United States Patent
Hsieh et al.

(10) Patent No.: US 7,338,171 B2
(45) Date of Patent: Mar. 4, 2008

(54) METHOD AND APPARATUS FOR VISUAL DRIVE CONTROL

(76) Inventors: Jen-Chuen Hsieh, No. 201, Sec. 2, Shih-Pai Road, Taipei (TW); Tzu-Chen Yeh, No. 201, Sec. 2, Shih-Pai Road, Taipei (TW); Yu-Te Wu, No. 201, Sec. 2, Shih-Pai Road, Taipei (TW); Po-Lei Lee, No. 201, Sec. 2, Shih-Pai Road, Taipei (TW); Li-Fen Chen, No. 201, Sec. 2, Shih-Pai Road, Taipei (TW)

( * ) Notice: Subject to any disclaimer, the term of this patent is extended or adjusted under 35 U.S.C. 154(b) by 725 days.

(21) Appl. No.: 10/695,562

(22) Filed: Oct. 27, 2003

(65) Prior Publication Data

US 2005/0088617 A1    Apr. 28, 2005

(51) Int. Cl.
*A61B 3/02* (2006.01)

(52) U.S. Cl. .................. 351/237; 351/239

(58) Field of Classification Search ......... 351/200, 351/205, 222, 237, 239, 243, 246
See application file for complete search history.

(56) References Cited

U.S. PATENT DOCUMENTS

| 4,493,539 A * | 1/1985 | Cannon, Jr. ............. 351/205 |
| 5,331,969 A * | 7/1994 | Silberstein ............. 600/544 |
| 2004/0087868 A1* | 5/2004 | Manahilov ............. 600/544 |
| 2004/0263780 A1* | 12/2004 | Hu et al. .............. 351/205 |

* cited by examiner

*Primary Examiner*—Huy Mai
(74) *Attorney, Agent, or Firm*—Christensen O'Connor Johnson Kindness PLLC

(57) ABSTRACT

In a method and apparatus for visual drive control, a set of flickering images that flicker at the same flicker frequency and that are associated with mutually distinct flicker patterns are simultaneously presented for viewing by an observer. Thereafter, evoked signals produced in the observer's brain are captured, and the flicker pattern having a greatest similarity with the captured evoked signals is determined. Finally, a control signal corresponding to the flicker pattern having the greatest similarity is generated.

11 Claims, 3 Drawing Sheets

METHOD AND APPARATUS FOR VISUAL DRIVE CONTROL

BACKGROUND OF THE INVENTION

1. Field of the Invention

The invention relates to a method and apparatus for drive control, more particularly to a method and apparatus for visual drive control.

2. Description of the Related Art

In U.S. Pat. No. 4,861,154, there is disclosed an apparatus for determining a display to which an observer is paying attention. The apparatus includes display means viewed by the observer and simultaneously producing images that flicker at different frequencies, detection means coupled to the observer by electrode means for contacting the observer's head, the detection means detecting the amplitude of evoked potentials produced in the observer's brain at the different frequencies, and comparison means operatively connected to the detection means and including means for storing amplitudes, the comparison means determining which amplitude is the largest, the largest amplitude indicating which of the display means is receiving the greatest amount of attention. The apparatus of the aforesaid patent is useful in measuring human attention in an advertising survey, in control systems, and in alarm intensity adjustment in alarm systems.

However, because the input to the comparison means in the aforesaid patent is in the frequency domain, Fourier conversion is necessary, which involves complex calculations and longer processing time.

SUMMARY OF THE INVENTION

Therefore, the object of the present invention is to provide a method and apparatus for visual drive control that can overcome the aforesaid disadvantages of the prior art.

According to one aspect of the present invention, there is provided a method for visual drive control, comprising the steps of:

a) simultaneously presenting a set of flickering images that flicker at the same flicker frequency and that are associated with mutually distinct flicker patterns for viewing by an observer;

b) capturing evoked signals produced in the observer's brain;

c) determining which one of the flicker patterns has a greatest similarity with the evoked signals captured in step b); and d) generating a control signal corresponding to said one of the flicker patterns determined in step c).

According to another aspect of the present invention, there is provided an apparatus for visual drive control, comprising:

display means for simultaneously presenting a set of flickering images that flicker at the same flicker frequency and that are associated with mutually distinct flicker patterns for viewing by an observer;

electrode means for capturing evoked signals produced in the observer's brain; and processing means, operatively connected to the electrode means, for determining which one of the flicker patterns has a greatest similarity with the evoked signals captured by the electrode means.

In the preferred embodiment, the processing means further generates a control signal corresponding to the flicker pattern determined thereby to have the greatest similarity with the evoked signals.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

It is known in the art that, when the human eye is stimulated by light, neurons associated with the human eye in the vision cortex region of the human brain will be activated accordingly. As a result, minute variations in electric and magnetic fields will be generated at the vicinity of the vision cortex region. These electric and magnetic field variations can be measured using known electroencephalography and magnetoencephalography techniques. Since brainwaves formed as a result of the electric and magnetic field variations have a rather high temporal resolution, activated neuron signals in the brain can be detected in real time.

The aforesaid activated neuron signals are also referred to as average evoked responses of the human brain. In general, an average evoked response is a variation in a brain wave that is of a specific waveform and that is generated by an area of the human brain as an indication of an action performed either voluntarily or involuntarily. In particular, visual evoked signals (VEP) and visual evoked fields (VEF) generated through visual stimuli of color br luminance are examples of average evoked responses. Brain waves are also characterized as having phase-locked and time-locked characteristics. "Phase-locked" means that an initial phase of the brain waves remains constant. "Time-locked" means that there is a constant time period between a time point when a stimulus is imposed and a time point when a brain wave is generated in response to the stimulus. From the foregoing, when flickering signals stimulate the human eye, the associated visual neurons will convert the light signals into electric signals that are transmitted to the human brain, and the vision cortex region of the human brain will generate brain waves corresponding to the electric signals.

Figure 1:
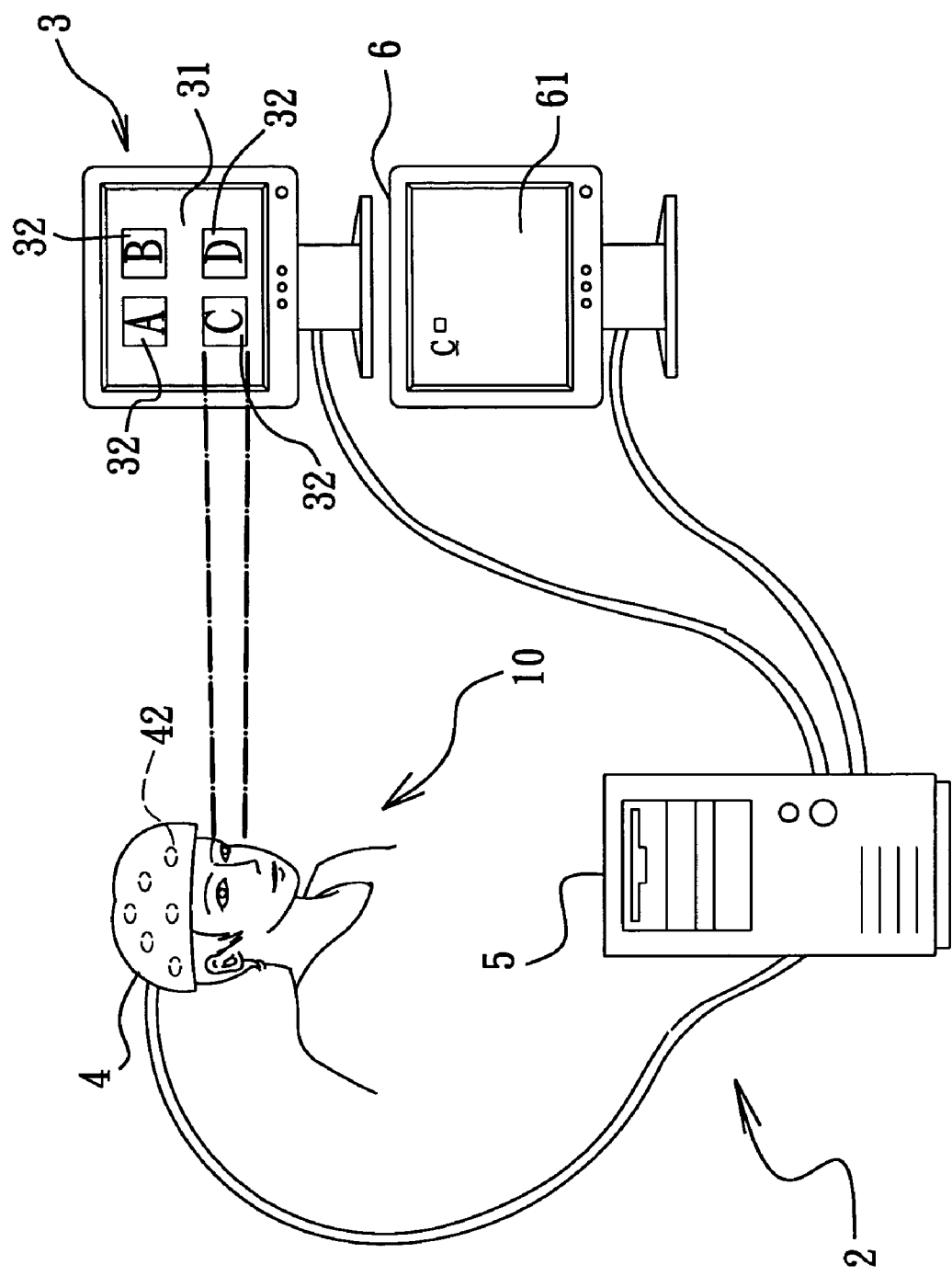
FIG. 1 is a schematic diagram illustrating the preferred embodiment of an apparatus for visual drive control according to the present invention.
Figure 2:
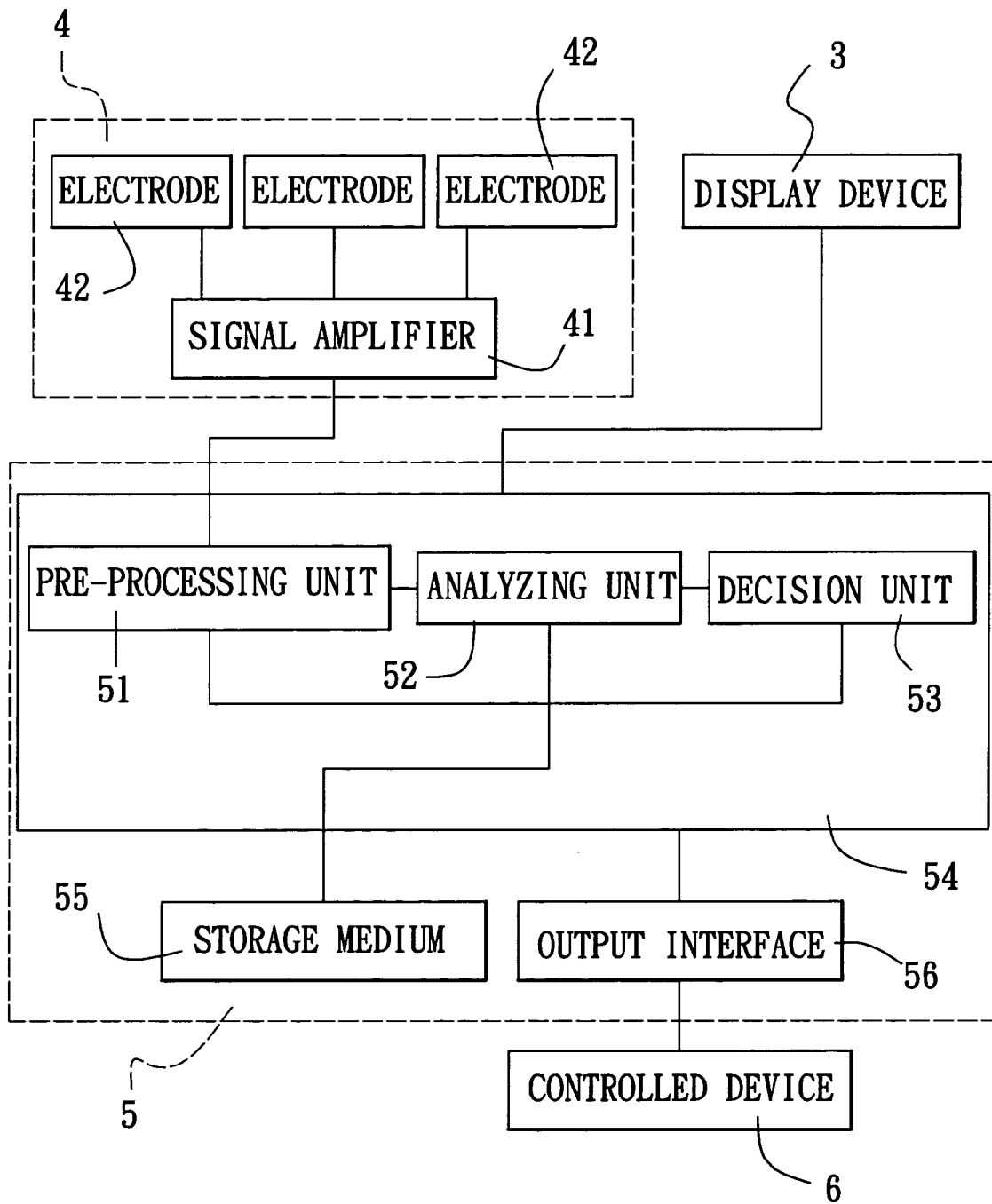
FIG. 2 is a schematic block diagram of the apparatus of the preferred embodiment.

Referring to FIGS. 1 and 2, the preferred embodiment of an apparatus 2 for visual drive control according to the present invention provides a display device 3 to be viewed by an observer 10, measures evoked signals produced by the observer's brain, and outputs a control signal in response to the measured evoked signals. The control signal can be used for the purpose of control or communication by the observer 10. The apparatus 2 includes the display device 3, an electrode device 4, and a processing device 5.

In this embodiment, the display device 3 is an LCD monitor coupled electrically to the processing device 5. However, it should be noted that the display device 3 is not limited to liquid crystal displays. Any device whose operating principle is based on direct light emanation or on light reflection, such as the combination of an image projector and a projector screen, can be used as long as light signals sufficient to stimulate the human eye can be presented to the observer 10.

In this embodiment, four images 32, marked respectively by the English letters A, B, C, D, are simultaneously presented on a screen 31 of the display device 3. The images 32 flicker at the same flicker frequency, and are associated with mutually distinct flicker patterns. It should be noted herein that the number of the images 32 and the content of the same can vary depending on actual requirements. For example, instead of the four letters A, B, C, D, intended operations, such as "dial a telephone number", "turn on light", "turn off TV", etc., can be used for the images 32. Moreover, the images 32 maybe designed to constitute a complete set of alphanumeric characters that forms a tool for writing, a car or airplane instrument panel for navigation control, etc.

The apparatus 2 of this invention is based on the "time-locked" characteristics of brain waves. As described in the foregoing, the time period defined in the "time-locked" characteristics of brain waves is constant. For the same observer, the duration of the time period is around 0.1 second. Thus, when a series of flickering signals stimulate the human eye, corresponding brain waves will be generated after the specific time period. In this embodiment, the flickering images 32 are associated with mutually distinct binary codes that control flashing of the images 32 at the same flicker frequency and that define the flicker patterns for the images 32. In this embodiment, the flicker frequency is 8 Hz, and each flicker pattern is repeated every one second. Moreover, for each one-second period, the flicker pattern consists of eight 0.125-second image frames. In the following illustrative example, the flicker patterns assigned to the letters A, B, C, D are 10110011, 10111110, 00100001, and 11110100, respectively, wherein "1" indicates a bright frame condition, and "0" indicated a dim frame condition.

The electrode device 4 in this embodiment is electroencephalography equipment suitable for measuring electric field variations of the human brain. The electrode device 4 includes a set of electrodes 42 for contacting the observer's head at locations adjacent to the vision cortex region of the human brain, and a signal amplifier 41 connected to the electrodes 42. The signal amplifier 41, which is coupled to the processing device 5, amplifies evoked signals picked-up or captured by the electrodes 42, and provides the same to the processing device 5. As evident to those skilled in the art, the aforesaid electroencephalography equipment may be replaced with magnetoencephalography equipment.

The processing device 5 includes a pre-processing unit 51, an analyzing unit 52, and a decision unit 53. The pre-processing unit 51 is coupled to the electrode device 4, and filters out noise and undesired components from the output of the electrode device 4. The analyzing unit 52 is coupled to the pre-processing unit 51, and analyzes the output of the pre-processing unit 51 to determine the similarity thereof with each of the flicker patterns. The decision unit 53 is coupled to the analyzing unit 52, receives similarity values calculated by the analyzing unit 52, and determines which one of the flicker patterns has a greatest similarity value. In the preferred embodiment, the decision unit 53 further compares the greatest similarity value with a predetermined threshold value. When the greatest similarity value is found to be smaller than the threshold value, the analyzing unit 52 will be enabled to analyze another set of evoked signals from the electrode device 4. Accordingly, when the greatest similarity value is determined to be larger than the threshold value, a control signal that corresponds to the flicker pattern with the greatest similarity value will be generated by the decision unit 53.

It is evident to those skilled in the art that the pre-processing unit 51 is not essential in the practice of the present invention, and that the analyzing unit 52 and the decision unit 53 can be integrated into a single unit. In this embodiment, the pre-processing unit 51, the analyzing unit 52 and the decision unit 53 are implemented using a single processor 54 connected to a storage medium 55 and an output interface 56. Accordingly, a controlled device 6 can be connected to the processor 54 through the output interface 56.

The storage medium 55 stores software that is to be executed by the processor 54, and a database containing the threshold value and a look-up table of the images, the flicker patterns and the control signals. Particularly, the software includes a display program for rendering the images 32, and an execution program that configures the processor 54 to execute operations of the pre-processing unit 51, the analyzing unit 52 and the decision unit 53. The execution program enables the processor 54 to output the control signal associated with the flicker pattern having the greatest similarity value as defined in the look-up table stored in the storage medium 55, i.e., the flicker pattern having the greatest similarity with the captured evoked signals. The control signal is then sent to the controlled device 6 through the output interface 56, which may be a wired interface, such as a cable wide-band network or Asymmetric Digital Subscriber Line (ADSL) network, or a wireless interface, such as one that complies with the Bluetooth protocol, the IEEE802.11 wireless protocol, or any mobile communications protocol applicable to cellular telephones. In the following illustrative example, the instructions assigned to the aforesaid flicker patterns 10110011, 10111110, 00100001, 11110100 are "show A", "show B", "show C", and "show D", respectively.

In the example of FIG. 1, the controlled device 6 is a computer monitor 61. In practice, any device that is capable of receiving control signals from the output interface 56 for performing operations intended by the observer 10 may be used as well, such as a printer, a telephone, an appliance switch, or remote equipment.

Figure 3:
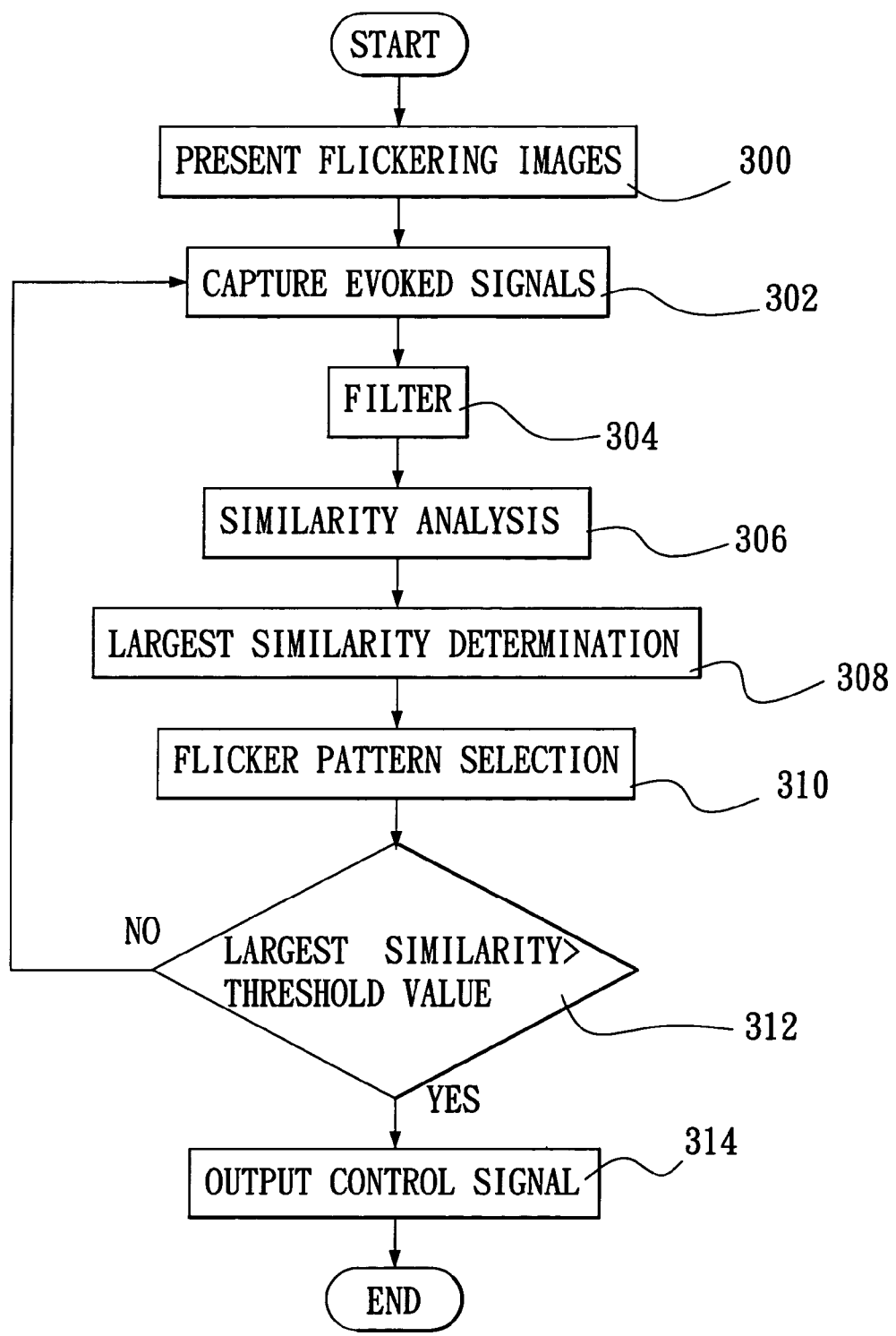
FIG. 3 is a flowchart to illustrate steps of the preferred embodiment of a method for visual drive control according to the present invention.

FIG. 3 is a flowchart to illustrate steps of the preferred embodiment of a method for visual drive control according to this invention.

In step 300, the set of flickering images 32 that flicker at the same flicker frequency and that are associated with mutually distinct flicker patterns are simultaneously presented on respective display regions of the screen 31 of the display device 3 for viewing by the observer 10.

In step 302, the electrode device 4 captures evoked signals produced in the observer's brain, and transmits the same to the processing device 5. Assuming that the observer 10 is paying attention to the image 32 that presents the letter "C", the captured evoked signals will be "0010000100100001 . . . ", wherein "1" indicates a bright frame condition, and "0" indicated a dim frame condition.

In step 304, the pre-processing unit 51 filters out noise and undesired components from the captured evoked signals.

In step 306, the analyzing unit 52 correlates the evoked signals with each of the flicker patterns.

In step 308, the decision unit 53 determines the greatest similarity value calculated by the analyzing unit 52, wherein the maximum similarity value is 100%.

In step 310, the decision unit 53 selects the flicker pattern corresponding to the greatest similarity value, i.e., the flicker pattern having the greatest similarity with the captured evoked signals.

In step 312, the greatest similarity value is compared with a predetermined threshold value, such as 95%. If the greatest similarity value is not smaller than the predetermined threshold value, the flow proceeds to step 314. Otherwise, the flow goes back to step 302.

In step 314, the decision unit 53 outputs the control signal that corresponds to the selected flicker pattern having the greatest similarity value with the evoked signals. Since the observer 10 is paying attention to the image 32 that presents the letter "C", and since the instruction associated with the flicker pattern for the letter "C" is "show C", the control signal for controlling the controlled device 6 to show the letter "C" thereon will be sent to the controlled device 6.

Since the flickering images 32 are associated with mutually distinct binary codes that define the flicker patterns, there can be as many as $2^8$ flicker patterns. That is, it is possible to present as many as $2^8$ flickering images 32 on the display device 3. By altering the flicker frequency and the number of bits in the binary codes, the number of flickering images 32 that can be presented simultaneously to the observer 10 can be increased accordingly. However, visual acuity will limit the actual number of flickering images 32 that can be implemented in practice. Particularly, the naked eye can usually distinguish two light source points spaced angularly apart by no less than a 45 second of arc. That is, when the distance between the observer and a light source is 60 cm, the two light source points cannot be spaced apart by a distance smaller than 2 cm so that the observer can distinguish between the same.

In sum, since the method and apparatus for visual drive control according to this invention uses images that flicker at the same flicker frequency for display, Fourier conversion is not required to result in fewer calculations and faster processing as compared to the prior art described hereinabove.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

We claim:

1. A method for visual drive control, comprising the steps of:
   a) simultaneously presenting a set of flickering images that flicker at the same flicker frequency and that are associated with mutually distinct flicker patterns for viewing by an observer;
   b) capturing evoked signals produced in the observer's brain;
   c) determining which one of the flicker patterns has a greatest similarity with said captured evoked signals; and
   d) generating a control signal corresponding to said one of said determined flicker patterns.

2. The method as claimed in claim 1, wherein said flickering images flicker at the same flicker frequency of about 8 Hz.

3. The method as claimed in claim 1, wherein said flickering images are associated with mutually distinct binary codes that control flashing of the flickering images at the flicker frequency and that define the flicker patterns for said flickering images.

4. The method as claimed in claim 1, wherein, in step c), the evoked signals are correlated with each of the flicker patterns to determine said one of the flicker patterns having the greatest similarity with the evoked signals.

5. The method as claimed in claim 1, wherein, step c) includes a sub-step of comparing the greatest similarity with a threshold value, the steps b) and c) being repeated when the greatest similarity is found to be smaller than the threshold value.

6. An apparatus for visual drive control, comprising:
   display means for simultaneously presenting a set of flickering images that flicker at the same flicker frequency and that are associated with mutually distinct flicker patterns for viewing by an observer;
   electrode means for capturing evoked signals produced in the observer's brain; and
   processing means, operatively connected to said electrode means, for determining which one of the flicker patterns has a greatest similarity with the evoked signals captured by said electrode means.

7. The apparatus as claimed in claim 6, wherein said flickering images flicker at the same flicker frequency of about 8 Hz.

8. The apparatus as claimed in claim 6, wherein said flickering images are associated with mutually distinct binary codes that control flashing of the flickering images at the flicker frequency and that define the flicker patterns for said flickering images.

9. The apparatus as claimed in claim 6, wherein said processing means correlates the evoked signals with each of the flicker patterns to determine said one of the flicker patterns having the greatest similarity with the evoked signals.

10. The apparatus as claimed in claim 6, wherein said processing means further generates a control signal corresponding to said one of the flicker patterns determined thereby to have the greatest similarity with the evoked signals.

11. The apparatus as claimed in claim 6, wherein said processing means includes a look-up table of the flicker patterns and control signals corresponding to the flicker patterns, said processing means further generating one of the control signals corresponding to said one of the flicker patterns determined by said processing means to have the greatest similarity with the evoked signals captured by said electrode means.

* * * * *